United States Patent [19]

Sterrett

[11] Patent Number: 4,933,418

[45] Date of Patent: Jun. 12, 1990

[54] STAIN-RESISTANT ORTHODONTIC DEVICE

[75] Inventor: Terry L. Sterrett, Long Beach, Calif.

[73] Assignee: Ormco Corporation, Glendora, Calif.

[21] Appl. No.: 230,759

[22] Filed: Aug. 10, 1988

[51] Int. Cl.$^5$ ............................................. C08G 18/42
[52] U.S. Cl. ........................................ 528/76; 528/77; 528/80; 528/83; 528/85; 433/11; 433/15; 433/18
[58] Field of Search ............... 528/76, 77, 80, 83, 528/85; 433/11, 15, 18

[56] References Cited

U.S. PATENT DOCUMENTS

| | | | |
|---|---|---|---|
| 3,530,583 | 9/1970 | Klein et al. | 433/11 |
| 3,741,918 | 6/1973 | Koleske et al. | 521/172 |
| 3,758,947 | 9/1973 | Kesling | 433/18 |
| 3,775,354 | 11/1973 | Hostettler et al. | 525/440 |
| 3,957,753 | 5/1976 | Hostettler | 560/189 |
| 4,038,753 | 8/1977 | Klein | 433/11 |
| 4,324,590 | 4/1982 | Schulz et al. | 106/35 |
| 4,412,820 | 11/1983 | Brummond et al. | 433/18 |
| 4,439,599 | 3/1984 | Watanabe et al. | 528/80 |
| 4,631,329 | 12/1986 | Gornowicz et al. | 528/28 |
| 4,748,192 | 5/1988 | Smith | 521/107 |
| 4,791,156 | 12/1988 | Hostettler | 528/76 |

Primary Examiner—Maurice J. Welsh
Attorney, Agent, or Firm—Marjama & Pincelli

[57] ABSTRACT

An elastomeric orthodontic tensioning device having improved stain resistance qualities.

12 Claims, 1 Drawing Sheet

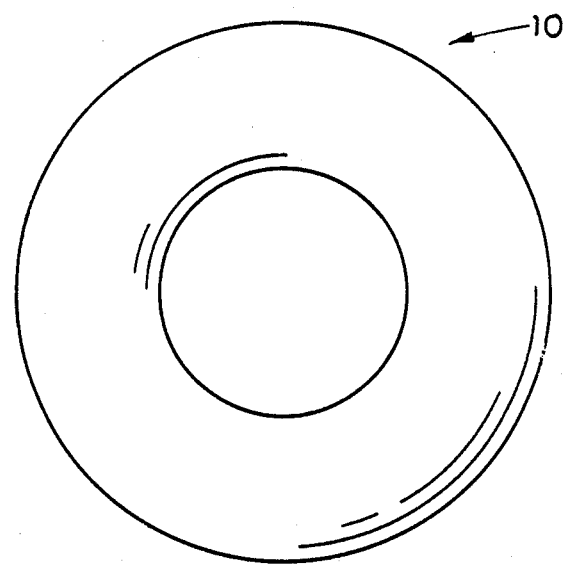
FIGURE

STAIN-RESISTANT ORTHODONTIC DEVICE

This invention relates to orthodontic elastomeric devices which are resistant to staining.

BACKGROUND OF THE INVENTION

It has long been an object in the orthodontic industry to improve the aesthetic properties of orthodontic devices. Recently it has become apparent that a great demand exists for orthodontic devices which have a minimal visual impact when viewed by others. As a result, a new generation of orthodontic brackets which are difficult to visually observe, have become much more available. An example of such devices are orthodontic brackets made out of a ceramic or crystalline material having a substantially clear color or a color substantially identical to the tooth. While such orthodontic devices have contributed significantly to improving the asthetic appearance of orthodontic brackets, the elastomeric orthodontic tensioning devices used therewith, such as elastomeric O-rings and chains, detract or diminish the improvements such devices have provided due to their staining and/or discoloration. Clinical experience has indicated that such ligatures and chains, which are typically made of thermoplastic urethane, take on a discoloration or stained appearance within one to two weeks after application of the device. This detracts substantially from the overall appearance and benefits provided by the orthodontic brackets. With aesthetic type orthodontic brackets, discolored or stained ligatures have become more noticeable. While it is known that certain thermosetting urethanes provide stain resistant qualities, these urethanes have been found to lack the necessary strength to be used as orthodontic ligatures.

Applicants have invented an orthodontic ligature which provides increased resistance to discoloration or staining and the strength necessary for use as an orthodontic device.

SUMMARY OF THE INVENTION

In the present invention, improved stain resistance is provided by making the orthodontic appliance out of a crosslinked polyurethane polymer having specific properties.

DESCRIPTION OF THE DRAWING

The FIGURE illustrates from elevation view of an orthodontic elastomeric ligature used to fasten an orthodontic arch wire to a orthodontic bracket made in accordance with the present invention.

DETAILED DESCRIPTION OF THE INVENTION

It is believed that there are two general forms of staining of elastomeric orthodontic devices. The first is believed to be due to the absorption and/or adsorption of components of the foodstuff which have similar solubilities to that possessed by the soft segment of the polyurethane elastomer. These components can be oils or fatty acids contained in the food. Such substances can readily be absorbed into the material and, subsequently, discolor due to denaturation or some similar oxidative process. Another possible aspect of such transient forms of staining is that substances which possess similar solubility to the elastomer can act as a carrier for colored species present in the food, which then deposit into the material and, consequently, color the material.

The second and more long-term aspect of staining is believed to parallel plaque formation on teeth. In general, it is believed, as with teeth, a thin proteinaceous pellicle is formed on the surface of the elastomer within the first twenty-four hours of usage. The formed pellicle is believed to then serve as a base for the further adsorption of proteins and other macromolecules. Proteinaceous surfaces are typically sticky and susceptible to denaturation due to changes in enviromental conditions. The sticky nature of such surfaces is naturally conductive to the adsorption of other materials (i.e., undigested foodstuff, fatty acids, etc.). Furthermore, the denaturation of proteins typically results in chemical species which are highly colored (yellow-brown) due to the ammoniacal nature of such compounds. It is, therefore, believed that the combined effect of protein denaturation and continued adsorption renders the elastomeric device discolored.

Referring to the Figure, there is illustrated an elastomeric orthodontic tensioning device 10 made in accordance with the present invention. In the particular embodiment illustrated, the orthodontic device 10 is an O-ring ligature used to secure an orthodontic bracket to an orthodontic arch wire. However, the elastomeric orthodontic tensioning device may comprise any other elastomeric device used in the mouth.

The orthodontic tensioning device 10 is made of a crosslinked thermosetting urethane. For the purpose of this invention a crosslinked urethane shall mean a urethane wherein the polymer chains are interconnected by covalent bonds. The urethane is preferably substantially clear or translucent so as to not substantially detract from the asthetic appeal of the orthodontic appliance to which it is applied. However, the present invention is not so limited. If desired, the orthodontic appliance may be made of any other color, for example, tooth colored.

The elastomeric orthodontic device 10 is preferably made of a thermosetting polyurethane formed by the reaction product having the following general formula.

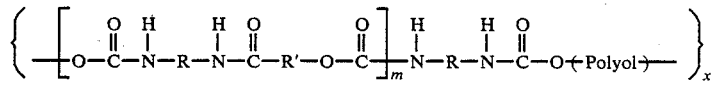

R—Represents any aromatic, alipathic or cycloaliphatic diisocyanate, e.g. 3,4-Toluene Diisocyanate (TDI), Methylyene Bis (P-Phenyl Diisocyanate) (MDI), 1,5Naphthalene Diisocyanate (NDI), Methylene Bis (P-cyclohexyl diisocyante (H$_{12}$MDI), Isophorone Diisocyanate (IPDI), etc.

R'—Represents any typical chain extends, ie. 1,4-Butanediol, Ethylene Diamine, Ethylene Glycol, etc.

Polyol—Represents any typical Polyl ie. Polytetramethylene Oxide (PTMO), Polycaprolactone, Polyethylene Adipate, etc.

The above reaction product is preferably obtained using a diamine crosslinking agent.

While thermosetting urethanes have recently been used for orthodontic elastomeric devices, however, such devices have provided unacceptable strength levels. Applicant has found that significant improvement in stain resistance can be improved by providing a urethane with specific properties. Stain resistance is improved by crosslinking a thermosetting polyurethane with an appropriate polyol. The resulting urethane should have a cross link density in the range of $5 \times 10^{-5}$ to $5 \times 10^{-4}$ moles/cm$^3$, preferably in the range of $1 \times 10^{-4}$ to $5 \times 10^{-4}$ moles/cm$^3$. The crosslink density being measured by swelling, as is more fully described in article by Bishop, E. T. & Davison, S., *Journal of Polymer Science*, Part C, Volume 26, page 59, 1969. To further resist staining through protein absorption, the critical surface tension of the device 10 is designed to be in the range of 20 to 40 Dynes/cm, preferably in the range of 20–35 Dynes/cm. The polyurethane is selected such that it provides a hydrolytically stable compound while at the same time provides increased surface hydrophylicity. The polyurethane should have a hydrolytic stability of no less than 70% of the initial tensile strength after 45 days submersion in a water or artificial saliva solution at 37° C., preferably no less than 95%. A suitable urethane utilizes a polycapolactonepolyol. The urethane also preferably has a glass transition temperature in the range of 50° to 80° C. and a ratio of soft segment to hard segment, as measured by electron spectroscopy for chemical analysis, in the range of 2.5/1 to 3.5/1. Such measurements can be obtained by using equipment sold by Physical Electronics model PHI 5100. An example of a suitable thermosetting polyurethane material for use with the present invention is sold by Acushnet Company of New Bedford, Mass. under the tradename E 417-0. The thermosetting polyurethane provides sufficient strength for using an orthodontic elastomeric device 10 yet was resistant to staining.

A device made in accordance with the present invention was compared for strength and stain resistance with devices made with a thermoplastic polyurethane and thermosetting polyurethane of the prior art.

The column marked relative rating is the stain resistance rating of devices used in patients mouth. The column identified as Yellowness index was conducted using a Hunter Laboratories Colormeter and the column identified by Protein absorption sets forth the protein absorption characteristic for each product.

With respect to relative rating as to stain resistances, this was based on a subjective evaluation by Orthodontists on devices used in a patients mouth. The higher the number the more resistant to staining. As can be seen the present invention showed significant improvement over the prior art thermplastic and thermosetting urethanes.

The Yellowness index was measured using the method as set forth in ASTM D1925-70. The products were placed in a mixture of 8 grams of yellow mustard with two (2) grams of distilled water for 30 minutes. The higher the number indicates the more yellow the product. The present invention provided better stain resistance than the prior art thermoset and theroplastic urethanes.

The hydroltic stability is an indication of the strength of the product after being submersed in a saliva solution. The prior art thermosetting material was totally inadequate wherein the present invention and prior art thermoplastic material illustrated excellent strengths.

The protein absorption test was conducted using radio labeled Bovine Albumim (I$^{125}$-Albumium, Bovine). A 2.35 mg/ml concentration in a phosphate buffer solution with pH adjusted to 7.4 is prepared. The sample was submersed in a 10 ml solution for a specified period of time (in the present invention about 8 hours). The it was rinsed, dried and counted using a sodium iodine, gama detector. A full discussion of the procedure used may be found in an article by Baszkin, A. and Lyman, DJ, *Journal of Biomedical Materials Research*, Vol. 14, p. 393, 1980. The higher the number, the more protein absorbed. The present invention had significant higher resistance to protein absorption over the prior art device.

The prior art thermoplastic material used was Dow Pellethane 2363-80A and the prior thermosetting material used was a Nihon Unipolymer urethane.

The results are as follows:

|  | Relative Rating | Yellowness Index | Hydroltic Stability | Protein Absorption |
| --- | --- | --- | --- | --- |
| Control Prior Art Thermosetting Polyurethane Device | 1.0 | 23 | 95% | 72 μg/cm$^2$ |
| Prior Art Thermoplastic Device | 1.5 | 36 | 10% | 20 μg/cm$^2$ |
| Device According to Invention | 2.5 | 20.8 | 95% | 8 μg/cm$^2$ |

It can be seen from the foregoing that the present invention not only results in improved stain resistance, but also provides the appropriate strength to function as an orthodontic tensioning device.

It is to be understood that while the present invention has set forth specific embodiments of the present invention, various modifications or changes may be made without departing from the scope of the present invention. While the present invention is particularly beneficial with respect to clear translucent orthodontic tensioning devices, it also has beneficial applications to orthodontic tensioning devices of other colors. The scope of the present invention being set forth by the following claims.

What is claimed is:

1. An orthodontic elastomeric tensioning device made of a thermosetting polyurethane which is crosslinked so as to form a hydrolytically stable composition, said thermosetting polyurethane having a crosslink density in the range of $5 \times 10^{-5}$ to $5 \times 10^{-4}$ mole/cm$^3$, said polyurethane is made using a polycaprolactone.

2. An orthodontic tensioning device according to claim 1 wherein said polyurethane is made using a polycaprolactone.

3. An orthodontic elastomeric tensioning device which comprises a polyurethane having a cross link density in the range of $5 \times 10^{-5}$ to $5 \times 10^{-4}$ mole/cm$^3$.

4. An orthodontic elastomeric tensioning device according to claim 3 wherein said polyurethane has a cross link density in the range of $1 \times 10^{-4}$ to $5 \times 10^{-4}$ mole/cm$^3$.

5. An orthodontic elastomeric tensioning device made of a thermosetting polyurethane having a crosslink density in the range of $5 \times 10^{-5}$ to $5 \times 10^{4}$ mole/cm³, said polyurethane is made using a polycaprolactone.

6. An orthodontic elastomeric tensioning device according to claim 5 wherein said device has a surface tension in the range of 25 to 35 Dynes/cm.

7. An orthodontic elastomeric tensioning device according to claim 5 wherein said polyurethane has a ratio of soft segment to hard segment in the range of 2.5/1 to 3.5/1.

8. An orthodontic elastomeric tensioning device according to claim 5 wherein said polyurethane has a glass transition temperature in the range of 50° C. to 80° C.

9. An orthodontic elastomeric tensioning device according to claim 1 wherein a diamine crosslinking agent is used to crosslink said polyurethane.

10. An orthodontic elastomer tensioning device according to claim 5 wherein said device is orthodontic O-ring.

11. An orthodontic elastomeric tensioning device according to claim 1 wherein said device is substantially clear or translucent.

12. An orthodontic elastoimeric tensioning device made of a crosslink polyurethane, said polyurethane is made using a polycaprolactone.

* * * * *